United States Patent [19]

Leshin

[11] 4,058,524

[45] Nov. 15, 1977

[54] PROCESS OF PREPARING AN AMINO THIAZOLYL DISULFIDE USING A WATER SOLUBLE SALT IN COMBINATION WITH WET 2,2-DITHIOBIS(BENZOTHIAZOLE)

[75] Inventor: Richard Leshin, Akron, Ohio

[73] Assignee: The Goodyear Tire & Rubber Company, Akron, Ohio

[21] Appl. No.: 648,085

[22] Filed: Jan. 12, 1976

Related U.S. Application Data

[63] Continuation-in-part of Ser. No. 470,239, May 15, 1974, abandoned.

[51] Int. Cl.$^2$ .......................................... C07D 417/12
[52] U.S. Cl. ........................................................ 544/136
[58] Field of Search ................................ 260/247.1 H

[56] References Cited

U.S. PATENT DOCUMENTS

| | | | |
|---|---|---|---|
| 2,837,519 | 6/1958 | Hardman | 260/247.1 |
| 3,150,130 | 9/1964 | Hardman | 260/247.1 H |
| 3,178,428 | 4/1965 | Eaker et al. | 260/247.1 H |
| 3,281,418 | 10/1966 | Budd et al. | 260/247.1 H |

Primary Examiner—Henry R. Jiles
Assistant Examiner—R. W. Ramsuer
Attorney, Agent, or Firm—F. W. Brunner; J. A. Rozmajzl

[57] ABSTRACT

In a known process for preparing 2-(4-morpholinodithio)-benzothiazole using 2,2'-dithiobis(benzothiazole) along with morpholine, sulfur, an inert organic solvent such as isopropyl alcohol and an oxidizing agent, the improvement wherein a water soluble salt in combination with wet 2,2'-dithiobis(benzothiazole) is substituted for dry 2,2'-dithiobis(benzothiazole).

10 Claims, No Drawings

PROCESS OF PREPARING AN AMINO THIAZOLYL DISULFIDE USING A WATER SOLUBLE SALT IN COMBINATION WITH WET 2,2-DITHIOBIS(BENZOTHIAZOLE)

This application is a continuation-in-part of application Ser. No. 470,239, filed May 15, 1974, and now abandoned.

This invention relates to a process of preparing 2-(4-morpholinodithio)-benzothiazole, MDB. More particularly this invention relates to the elimination of a drying step in the preparation of MBTS for use as a reactant in the preparation of MDB.

MDB is known as both an accelerator for the sulfur vulcanization of rubber and as a vulcanizing agent of rubber. The reaction involving MBTS and/or the parent 2-mercaptobenzothiazole, MBT, morpholine, sulfur, isopropyl alcohol and an oxidizing agent to prepare MDB is well known in the art (U.S. Pat. No. 3,281,418). From a commercial standpoint, it is desirable that process costs be as low as possible. Both MBT and MBTS are generally prepared in aqueous systems. It has recently been revealed that wet MBT filter cake, obtained from the corresponding aforementioned slurry, may be used to make MDB without intermediate drying (U.S. Pat. No. 3,780,038). When MDB is made from MBTS, the prior art teaches the use of dry MBTS which is obtained by filtering the corresponding aforementioned slurry and drying the filter cake. U.S. Pat. No. 3,780,038 indicates that the system containing wet MBTS had a lower tolerance to water than a system containing wet MBT, (column 2, lines 2 to 5). If wet MBTS could be used in the preparation of MDB, the drying step used in the preparation of the MBTS could be eliminated. Although the prior art teaches the use of dry MBTS in the manufacture of MDB, no mention is made of the use of the wet forms of this compound. Presumably those responsible for the prior art believed that the presence of an excess amount of water resulted in decreased yield and purity.

It is an object of the present invention to provide an economical process for preparing MDB. It is another object of this invention to use wet MBTS in combination with a water soluble salt in the preparation of MDB in high yields and high purities.

The objects of this invention are accomplished by reacting wet MBTS in combination with a water soluble salt along with morpholine and sulfur using an inert organic solvent, preferably an aliphatic alcohol having 3 to 5 carbon atoms, as a vehicle in the presence of an oxidizing agent to produce MDB in satisfactory yield and purity.

Since the MBTS is normally prepared in aqueous systems, the present process permits the use of moist filter cakes of said compounds thereby eliminating a drying step in their preparation.

In U.S. Pat. No. 3,281,418, the contents of which are incorporated by reference, the mixture of morpholine, sulfur, an inert organic solvent and the MBTS must be heated to a temperature above the crystallization point of said mixture before the oxidizing agent is added and the oxidizing agent must be added prior to the crystallization of any of the MDB. In the example in said patent where MBTS is used (Example 1), the MBTS is dry. In the present process wet MBTS in combination with a water soluble salt is used, the mixture need not be heated to a temperature above its crystallization point, and the oxidizing agent need not be added prior to crystallization of the MDB.

The present process is ideally suited for the use of MBTS which has been prepared in an aqueous system where the MBTS is formed as an aqueous slurry and is subsequently separated from said slurry, for example, by filtration. The process is also suited for the use of dry MBTS to which water is added for purposes of forming a slurry requiring lesser volumes of the inert organic solvent, while still maintaining the slurry sufficiently fluid to enable the reactants to be readily agitated. The wet MBTS can have a moisture content of from 20 to 65 percent, i.e., the water content of the MBTS can be from 25 to 186 parts by weight of water per 100 parts by weight of MBTS. Centrifugal filtration can result in a moisture content of less than 50 percent. It is preferred that the water content of the wet MBTS be from about 20 percent to 60 percent, i.e., from 25 to 150 parts of water per 100 parts by weight of MBTS, most preferably about 40 (66.7 parts of water) to about 55 percent (122 parts of water) by weight, and that the salt be in sufficient amount to saturate the total water present after the addition of the oxidizing agent. In all cases the amount of water in combination with the MBTS of the present process is never less than 20 percent nor more than 65 percent. In addition, the total water content of the mixture of morpholine, sulfur, solvent, salt and wet MBTS can never exceed 186 parts by weight of water per 100 parts by weight of dry MBTS, preferably does not exceed 150 parts, and most preferably never exceeds 122 parts.

The present process can be carried out in either a batchwise or continuous fashion. In either case the morpholine, sulfur, solvent, salt and wet thiazole are combined to form a combination which is then combined with the aqueous oxidizing agent. In the batchwise process, the aqueous solution of the water soluble oxidizing agent is normally added to the combination under agitation. In the continuous process the combination and the aqueous solutions are combined continuously.

The salt is combined with the reactants and solvent before the reaction begins, i.e., before the addition of the oxidizing agent. The salt is added in solid form in sufficient quantity to be at least 50 percent of the amount needed to saturate the water content of the wet MBTS at room temperature, that is, about 25° C. The preferred amount is at least 100 percent of that necessary to saturate the aqueous portion of the reaction mixture at the temperature of the mixture just prior to the addition of the oxidizing agent. The most preferred amount is enough to totally saturate the entire aqueous phase including the water added with the oxidizing agent at the reaction temperature during the addition of the oxidizing agent. The salt may be added at ambient temperature or at any temperature up to and including that of the boiling point of solvent. When isopropyl alcohol is the solvent, the boiling point would be approximately 82° C. It is preferred that the salt is added during the initial mixing of reactants at ambient temperatures. The amount of salt depends upon its solubility in water. It is preferred that enough salt is added to saturate the aqueous phase including the water of the solution of the oxidizing agent which is added during the reaction.

Batch reactions indicate that preferably 5 to 15 percent excess sulfur, 10 to 20 percent excess morpholine and 10 to 30 percent excess oxidizing agent are used. By "excess" is meant the percent of a reactant charged beyond that required for exact stoichiometry. Naturally optimum conditions will possibly vary depending on such factors as reactor size, degree of agitation and whether the reaction is of batchwise or continuous nature.

The following examples illustrate the preparation of 2-(4-morpholinodithio)-benzothiazole using wet MBTS without salt.

EXAMPLE 1

The following reactants were reacted as described below.

| Ingredients | Grams |
|---|---|
| MBTS | 33.6 |
| Water | 33.6 |
| Morpholine (15% excess) | 20.0 |
| Sulfur (6% excess) | 6.8 |
| 2-Propanol/H$_2$O Azeotrope | 37 |
| 2.24 Molar Aqueous Sodium Hypochlorite (15% excess) | 51.4 ml. |

The MBTS and water simulate a 50 percent wet MBTS filter cake. These were combined with the morpholine, sulfur and 2-propanol/water azeotrope and heated to reflux. The cloudy mixture was cooled to 59° C. and the hypochlorite solution was added in 3 minutes. Within 4 minutes of stirring the oily precipitate had solidified. The slurry was cooled to 30° C. and 600 milliliters of water was added. The solid product was filtered and washed with water. The product was then dried in air. The yield was 52.7 grams (92.6%). The melting point was 104°–108° C. The purity was 90.7 percent. The true yield was as follows.

$$(.926)(.907)(100) = 84.0\%$$

The product of Example 1 is typical of the low purity and quality of products derived from MBTS in the presence of excessive amounts of water.

EXAMPLES 2 TO 11

Examples 2 to 4 illustrate the effect of other amounts of water and examples 5 to 11 illustrate the effects of water and various water soluble salts on yield and purity. As in Example 1, MBTS and water were mixed to simulate wet MBTS. The procedures and amounts (except for water where noted) and the presence of salts as shown were the same as in Example 1. The salts were added with the initial reactants.

| Ex. | Water Grams | Water Percent | Salt Type | Salt Grams | Product Yield (%) | Product Purity (%) | True Yield[1] (%) |
|---|---|---|---|---|---|---|---|
| 2 | 14.2 | 30 | — | — | 96.5 | 89.3 | 86.2 |
| 3 | 22.4 | 40 | — | — | 92.2 | 87.6 | 80.8 |
| 4 | 41.0 | 55 | — | — | 90.7 | 91.0 | 82.6 |
| 5 | 22.4 | 40 | Na$_2$SO$_4$ | 16.8 | 95.5 | 90.9 | 86.8 |
| 6 | 33.6 | 50 | Na$_2$SO$_4$ | 29.4 | 99.6 | 92.8 | 92.4 |
| 7 | 33.6 | 50 | NaCl | 25.5 | 97.9 | 94.3 | 92.3 |
| 8 | 41.0 | 55 | NaCl | 12.1 | 97.1 | 94.6 | 91.9 |
| 9 | 41.0 | 55 | NaCl | 17.5 | 96.5 | 91.3 | 88.1 |
| 10 | 41.0 | 55 | KCl | 22.4 | 95.6 | 91.0 | 87.0 |
| 11 | 41.0 | 55 | Ca Acetate | 22.4 | 93.6 | 95.1 | 89.0 |

[1]True Yield = $\frac{(Yield)(Purity)}{100}$

Examples 5 to 11 are within the scope of the invention. When less than 40 percent water on the MBTS was present, as in Example 2, the results were marginally acceptable. The salts can be the water soluble salts of sodium, potassium, lithium, calcium, magnesium, etc. and can be acetates, carbonates, mono, di or tribasic phosphates, sulfates, nitrates, halides and benzoates. By water soluble salt is meant a salt with a solubility of at least 5 grams per hundred grams of water, and preferably at least 10 grams per hundred grams of water. Illustrative of the salts, but not limiting, are the following examples.

sodium acetate
sodium carbonate
sodium phosphate
sodium mono hydrogen phosphate
sodium di hydrogen phosphate
sodium sulfate
sodium nitrate
sodium chloride
sodium bromide
sodium benzoate Potassium and lithium salts containing the above cations, e.g., potassium sulfate and lithium sulfate, further illustrate the water soluble salts.

calcium acetate
calcium nitrate
calcium chloride
calcium bromide
calcium iodide

Magnesium salts containing the above cations, e.g., magnesium acetate and magnesium chloride, further illustrate the water soluble salts.

Salts such as magnesium carbonate, calcium sulfate and calcium carbonate are not water soluble salts as defined herein and therefore are not intended to be used in the practice of the present invention.

Any of the above water soluble salts could be substituted for the water soluble salts in working examples 5 to 11 to provide increased yields and/or purities.

It should be noted that either the hydrates or anhydrides of the above salts can be used.

The water soluble salt is a compound other than the oxidizing agent and must not adversely interact with the oxidizing agent or the product of the reaction. For example, Na$_2$S can not be used since it will react with oxidizing agents as well as the product of the reaction.

In defining the salt as a salt with a solubility of at least 5 grams per 100 grams of water and preferably at least 10 grams per 100 grams of water, the solubility is the solubility at 25° C.

While certain representative embodiments and details have been shown for the purpose of illustrating the invention, it will be apparent to those skilled in this art that various changes and modifications may be made therein without departing from the spirit or scope of the invention.

What is claimed is:

1. A process of preparing 2-(4-morpholinodithio)-benzothiazole comprising combining a mixture of morpholine, sulfur, an inert organic solvent, a water soluble salt, and wet 2,2'-dithiobis(benzothiazole) with an aqueous solution of a water soluble oxidizing agent wherein the wet 2,2'-dithiobis (benzothiazole) contains 25 to 186 parts by weight of water per 100 parts by weight of 2,2'-dithiobis(benzothiazole), with the proviso that the maximum water level in the morpholine, sulfur, solvent 2,2'-dithiobis(benzothiazole) mixture, prior to combining the mixture with the oxidizing agent, is 186 parts by weight of water per 100 parts by weight of 2,2'-dithiobis (benzothiazole), and wherein the water soluble salt is present in an amount sufficient to constitute at least 50 percent of the amount of salt necessary to saturate the water content of the wet 2,2'-dithiobis(benzothiazole) at 25° C., wherein the water soluble salt is soluble to the extent of at least 5 parts by weight per 100 parts by weight of water at 25° C. wherein the water soluble salt is a compound other than the oxidizing agent and is incapable of adversely reacting with the oxidizing agent and the 2-(4-morpholinodithio)-benzothiazole.

2. The process according to claim 1 wherein the 2,2'-dithiobis(benzothiazole) is in the form of a filter cake.

3. The process according to claim 1 wherein the process is continuous, the morpholine, sulfur, thiazole and solvent being in one stream and the water soluble oxidizing agent being in an aqueous stream, the two streams being combined continuously.

4. The process according to claim 1 wherein the solvent is an aliphatic alcohol containing 3 to 5 carbon atoms.

5. The process according to claim 1 wherein the solvent is isopropyl alcohol and the water soluble oxidizing agent is sodium hypochlorite.

6. The process according to claim 1 wherein the wet 2,2'-diothiobis(benzothiazole) contains 25 to 150 parts by weight of water per 100 parts by weight of the 2,2'-dithiobis(benzothiazole) and wherein the total water level in the mixture does not exceed 150 parts by weight of water per 100 parts by weight of 2,2'-diothiobis(benzothiazole).

7. The process according to claim 1 wherein the wet 2,2'-dithiobis(benzothiazole) is the wet separated product resulting from the preparation of 2,2'-dithiobis (benzothiazole) in an aqueous system to form an aqueous slurry from which the 2,2'-dithiobis(benzothiazole) is separated.

8. The process according to claim 1 wherein the cationic portion of the water soluble salt is selected from the group consisting of sodium, potassium, lithium, calcium and magnesium and the anionic portion of the salt is selected from the group consisting of acetate, carbonate, monobasic phosphate, dibasic phosphate, tribasic phosphate, sulfate, nitrate, halide and benzoate radicals.

9. The process according to claim 8 wherein the water soluble salt is selected from the group consisting of sodium sulfate, sodium chloride, potassium chloride and calcium acetate.

10. The process according to claim 8 wherein the water soluble salt is sodium chloride or sodium sulfate.

* * * * *